US00PP21767P3

(12) United States Plant Patent
Merritt

(10) Patent No.: US PP21,767 P3
(45) Date of Patent: Mar. 8, 2011

(54) LILY PLANT NAMED 'BJM 005'

(50) Latin Name: ***Lilium asiatic*×*L. longiflorum* hybrid**
Varietal Denomination: BJM 005

(75) Inventor: Richard H. Merritt, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 200 days.

(21) Appl. No.: 12/287,591

(22) Filed: Oct. 10, 2008

(65) Prior Publication Data

US 2010/0095417 P1 Apr. 15, 2010

(51) Int. Cl.
*A01H 5/00* (2006.01)

(52) U.S. Cl. ..... Plt./314

(58) Field of Classification Search ..... Plt./314
See application file for complete search history.

(56) References Cited

U.S. PATENT DOCUMENTS

PP16,360 P2 * 3/2006 Mak ..... Plt./314

* cited by examiner

*Primary Examiner*—Wendy Haas
(74) *Attorney, Agent, or Firm*—Klarquist Sparkman, LLP

(57) ABSTRACT

A new and distinct lily plant substantially as shown and described, characterized by (1) stem thickness supported by flower crown without bending (10-11 mm in diameter); (2) straight stems with even leaf distribution from bottom to top (95-115 leaves per plant); (3) flower crown compact; (4) flower sizes (11 cm long 6 cm wide at open stage); (5) continuous blooms for two to four weeks; (6) coloration of leaves uniform from bottom to top; (7) height of plant around 40 cm; and (8) red to purple flowers.

6 Drawing Sheets

Latin name of the genus and species of the plant claimed: *Lilium asiatic*×*L. longiflorum* hybrid.

Botanical name—variety denomination: 'BJM 005'.

CROSS REFERENCE TO RELATED APPLICATIONS

This application is related to U.S. application Ser. No. 12/287,592.

STATEMENT REGARDING FEDERALLY SPONSORED RESEARCH OR DEVELOPMENT

None.

FIELD

The present invention comprises a new and distinct cultivar of *Lilium* cv named 'BJM 005' characterized by numerous red to purple flower crowns on strong stems with rich green foliage. This cultivar is winter hardy, sprouts freely and can provide a garden/specimen plant of up to 10 blooms.

SUMMARY

A new and distinct cultivar of *Lilium asiatic*×*L. longiflorum* hybrid named 'BJM 005' substantially as herein shown and described in FIGS. 1-6. The parentage of the *longiflorum* variety is not known; the parentage of the *asiatic* is 'Little Missy' (unpatented). The variety was developed as part of a breeding program in New Brunswick, N.J.

The new variety is characterized by numerous large red to purple flower crowns on short straight strong stems with rich green plentiful foliage. The following traits have been repeatedly observed in asexually propagated progeny and are determined to be the basic characteristics of this invention which in combination distinguish this lily as a new and distinct cultivar: (1) stem thickness supported by flower crown without bending (10-11 mm in diameter); (2) straight stems with even leaf distribution from bottom to top (95-115 leaves per plant); (3) flower crown compact; (4) flower sizes (11 cm long 6 cm wide at open stage); (5) continuous blooms for two to four weeks; (6) coloration of leaves uniform from bottom to top; (7) height of plant around 40 cm; and (8) red to purple flowers. To the inventor's knowledge, there are no other cultivars of lily of this size of plant or in terms of the superior plant and flower quality in the market.

'BJM 005' has been asexually reproduced by tissue culture using bulb scale in New Brunswick, N.J. No evidence of off-types of 'BJM 005' have been observed or reported to us. Thus, it is concluded that 'BJM 005' is stable and reproduces true to type in successive generations of asexual reproduction.

The following detailed description concerns the variety 'BJM 005'. Progeny of the original plant have been observed growing in cultivated areas in New Brunswick, N.J. Certain characteristics of this variety, such as growth and color, may change with changing environmental conditions (such as light, temperature, moisture, nutrient availability, soil or other factors). Color descriptions and other terminology are used in accordance with their horticultural descriptions, unless the context clearly indicates otherwise. Color designations are made with reference to the Munsell Color Charts for Plant Tissues.

Figure 1:
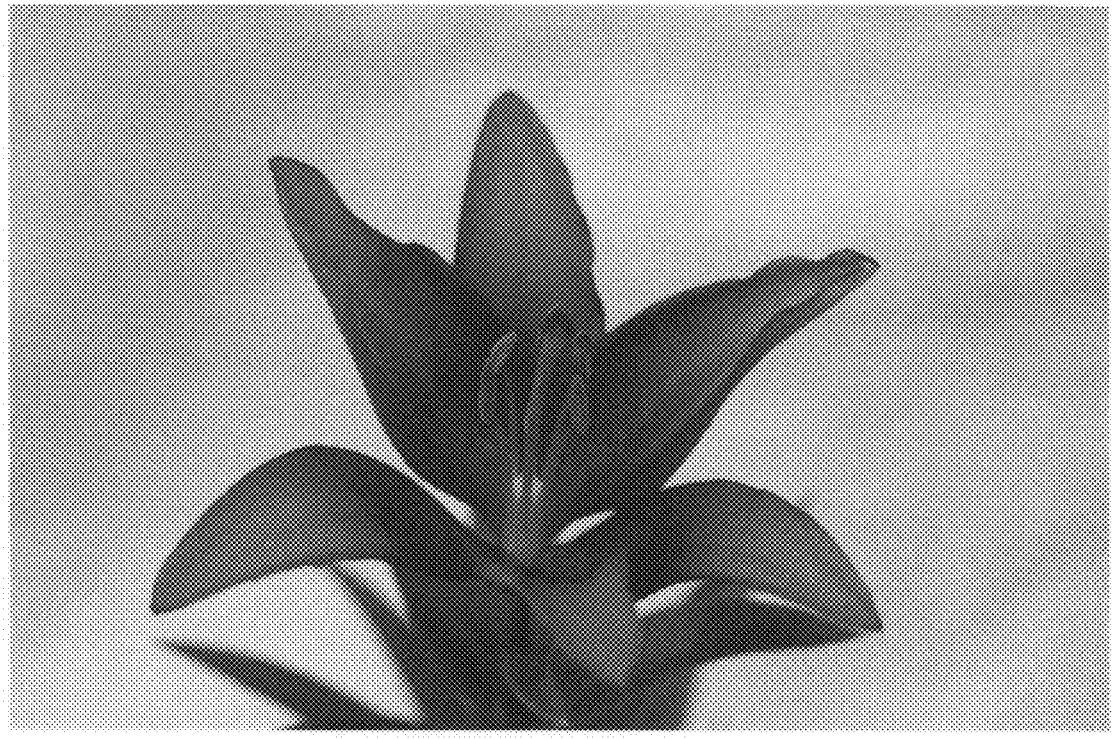
FIGS. 1-4 are photographs showing a close-up of the flowers of the new variety.
Figure 2:
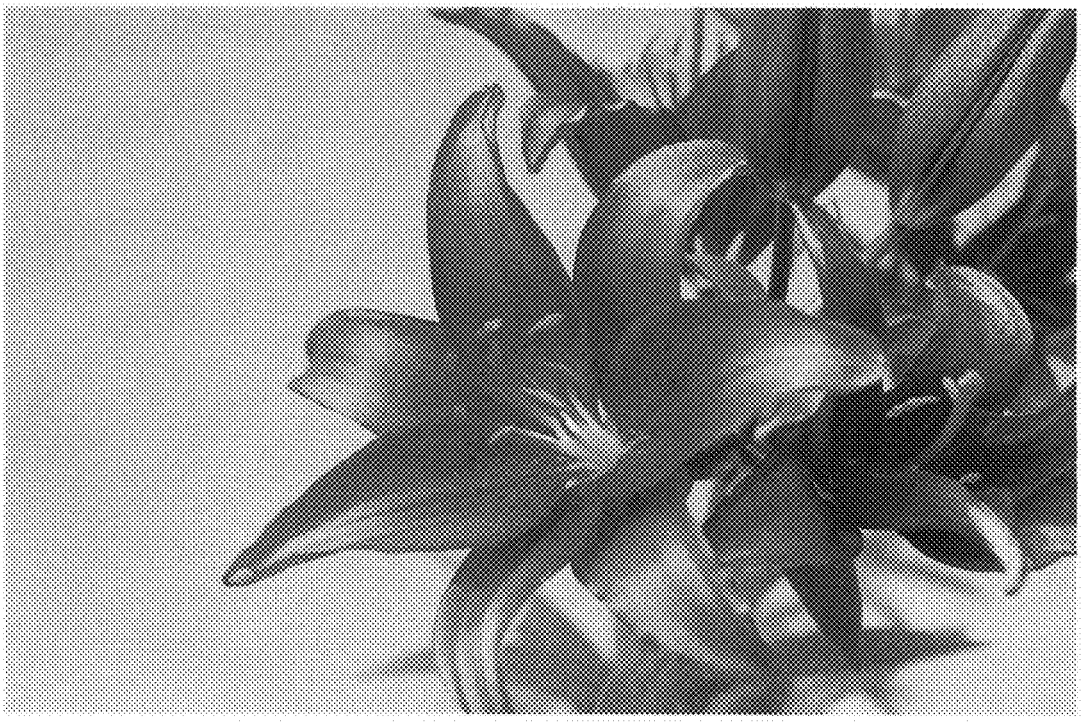
Figure 3:
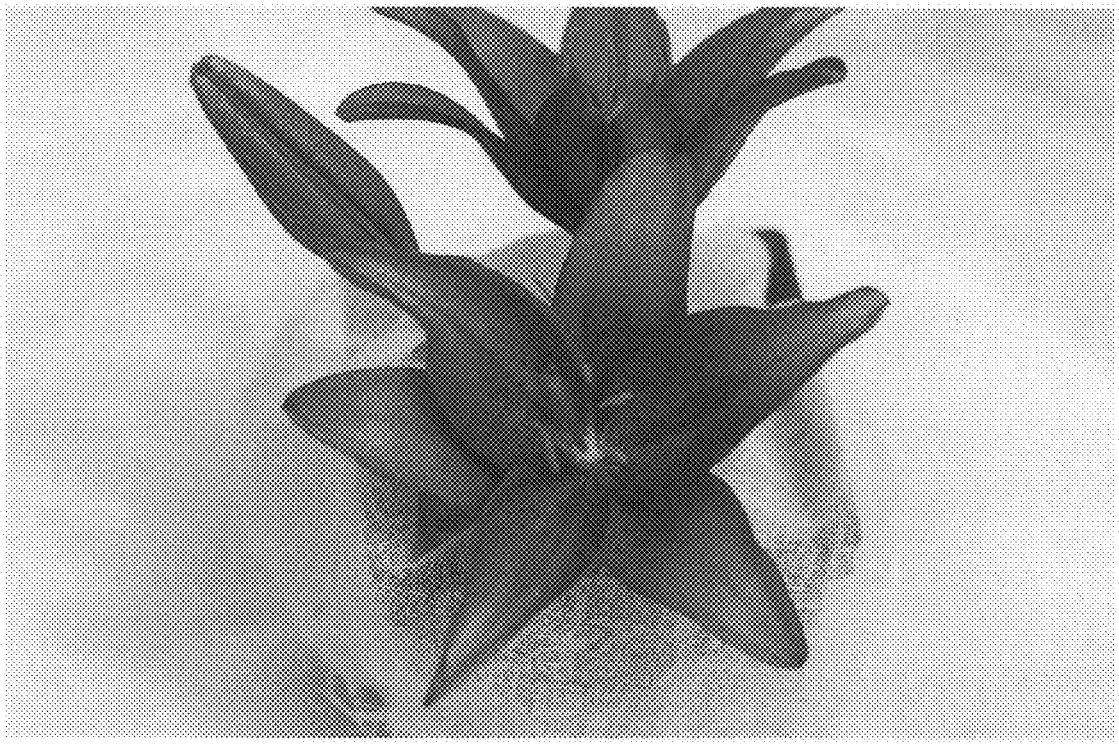
Figure 4:
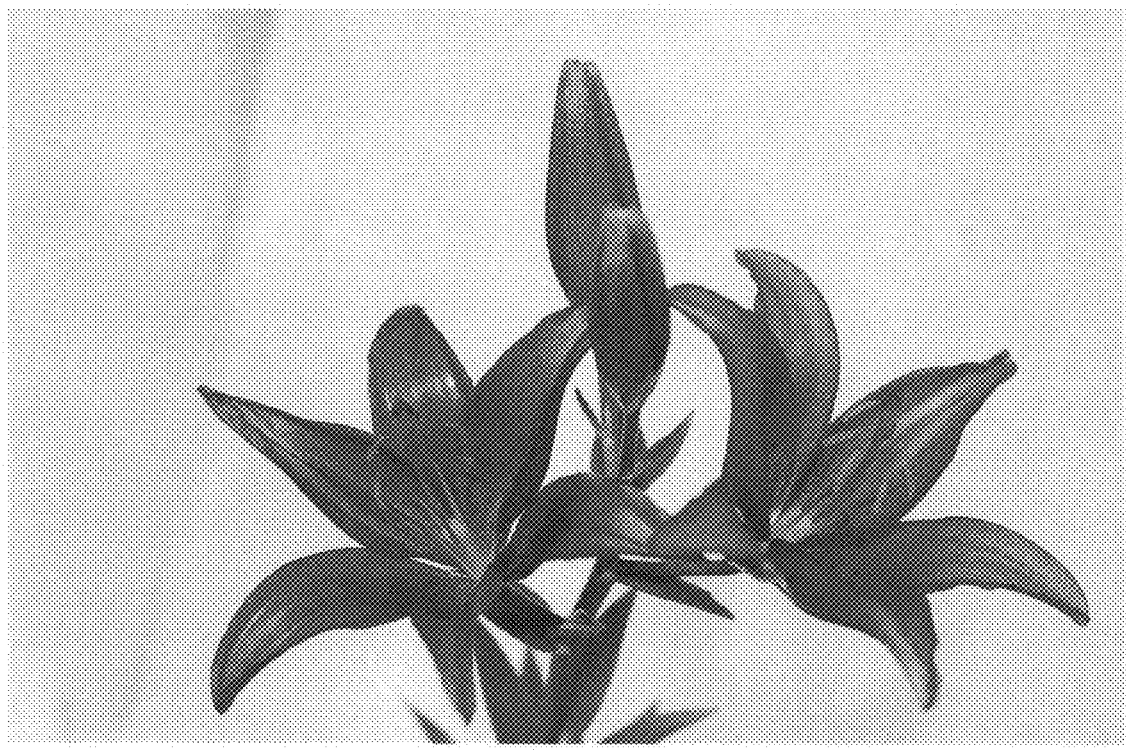
Figure 5:
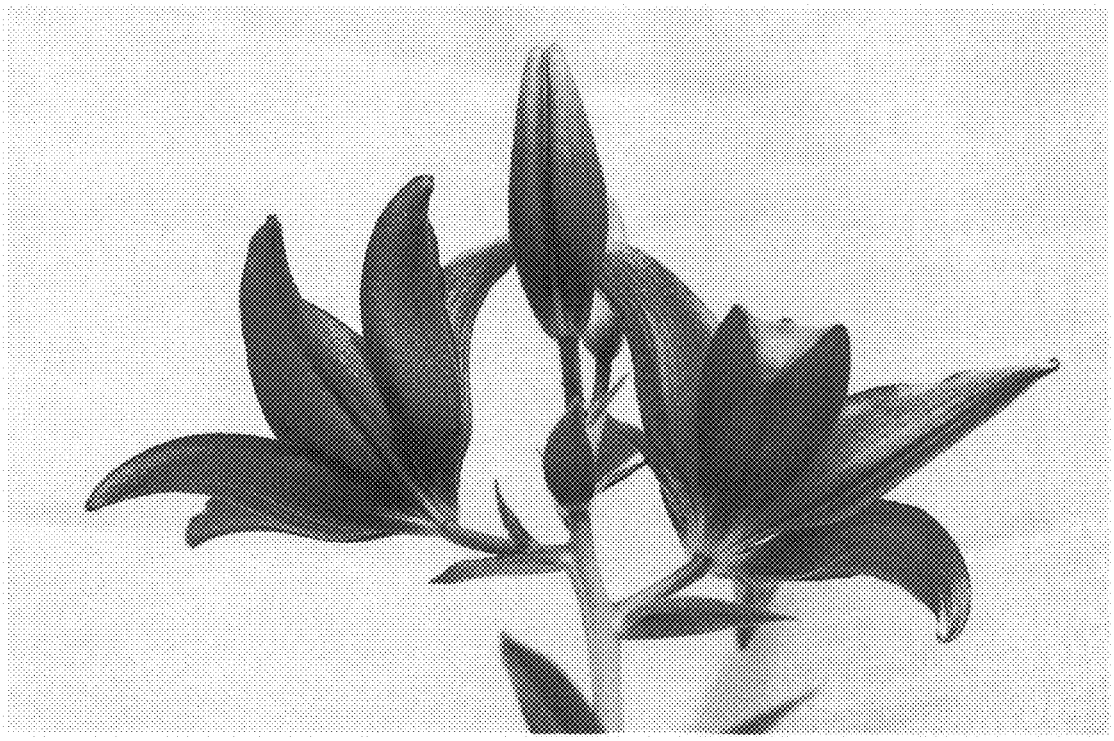
FIG. 5 is a photograph showing a close-up of the stem of the new variety.
Figure 6:
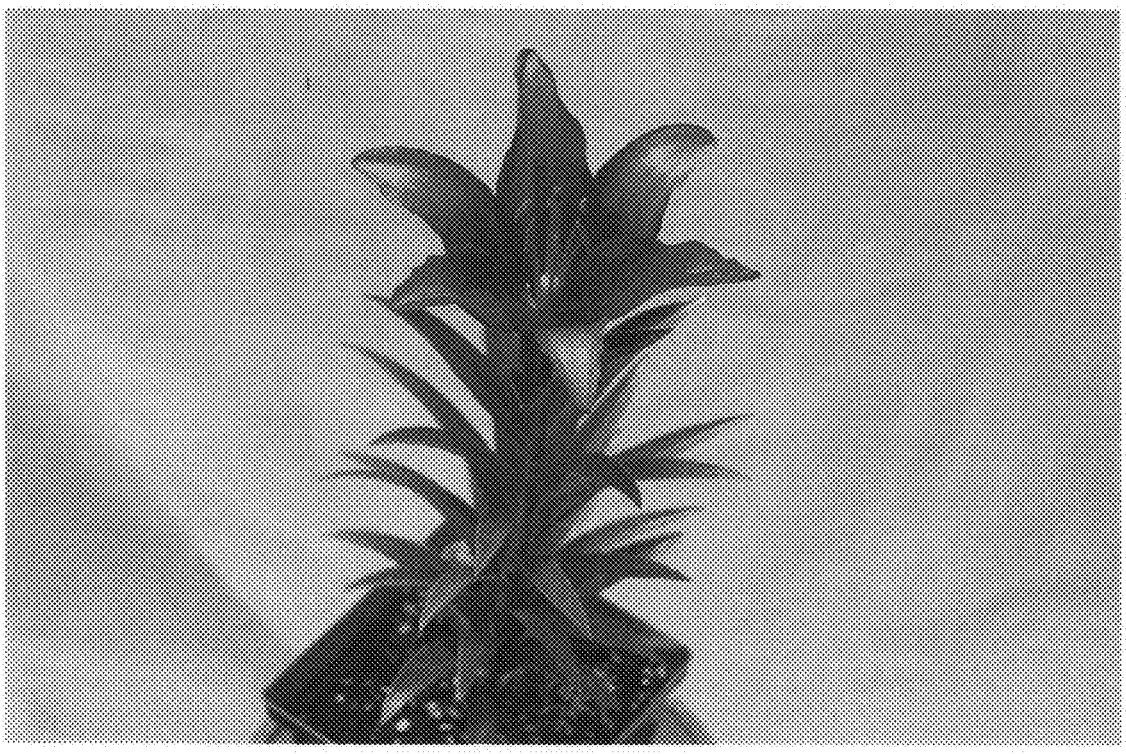
FIG. 6 is a photograph showing the stalk and leaves of the new variety.

The colors of an illustration of this type may vary with lighting and other conditions and, therefore, color characteristics of this new variety should be determined with reference to the observations described herein, rather than from this illustration alone.

BOTANICAL DESCRIPTION

The following is a detailed description of the invention based on lily plant 'BJM 005' produced under asexual reproduction by tissue culturing. Characteristics based on observations of a nine-month-old plant.

I. Relating to the plant:

*Origin.*—New Brunswick, N.J.

*Parentage.*—*Lilium Asiatic* 'Little Missy'×*L. longiflorum* hybrid.

*Seed parent.*—*L. Asiatic* 'Little Missy'.

*Pollen parent.*—*L. longiflorum* hybrid.

*Commercial classification.*—Bedding, specimen plant.

*Classification.*—Division 5, according to the Horticultural Classification of Lilies by The Royal Horticultural Society of London.

*Height.*—Approximately 40 cm from the top of the soil to the top of the flowers from bulbs of 14 cm in circumference.

*Stem color.*—Green-yellow Munsell 5 GY, V5/C6.

*Stem diameter.*—10 mm to 11 mm.

*Foliage.*—95-115 leaves.

*Leaf arrangement.*—Staggered upright.

*Leaf size.*—Approximately 9.5 cm to 10.2 cm long 1.5 cm wide.

*Texture.*—Glossy smooth.

*Color.*—Green-yellow Munsell 7.5GY V4/C4.

*USDA Zone.*—Winter hardy to USDA zone 6.

II. The bud:

*Size.*—8 cm long and 2.5 cm to 3 cm wide just prior to opening.

*Color.*—Red-purple — 5RP V4/C10 Munsell.

III. The flower:

*Blooming habit.*—Terminal inflorescence.

*Days to bloom.*—Flowers approximately 90 days after spring greenhouse planting (70-78° F. during the day, 60-70° F. at night) under typical commercial flower forcing conditions of 16° Celsius night time temperatures.

*Inflorescence size.*—Approximately 11 cm high and 6 cm wide when there are 3 flowers present.

*Flower size.*—Large.

*Diameter.*—Approximately 12.5 cm.

*Depth.*—Approximately 7 cm.

*Shape.*—Cupped inward, flares at top.

*Tepal number.*—6.

*Texture.*—Matte smooth inside; glossy smooth outside.

*Color.*—Red-purple — Edging — 5RP V3/C6, inner — 5RP V4-5/C8-10 Munsell.

*Fragrance.*—Slight.

*Length.*—Approximately 2 cm.

IV. The reproductive organs:

*Anthers.*—6 in number.

*Anthers before dehiscence.*—Approximately 1 cm. Color: yellow-red — Munsell 2.5YR, V3/C6.

*Filaments.*—Length: approximately 4.5 cm. Color: red-purple — Tip 5RP V4/C8, fades to 5RP V7/C4 Munsell.

*Pollen.*—Color: Yellow-violet — 2.5Y V8/C10 Munsell.

*Pistil.*—1 in number, exserted beyond stamens.

*Style.*—Length: approximately 4.3 cm. Color: red purple — 5RP V5-C10 Munsell.

*Stigma.*—Color: red-purple — 5RP, V3/C6 Munsell.

V. The fruit:

*Fertility.*—None.

TABLE 1

Comparison of 'BJM 005' to other varieties

| | Parent *L. Asiatic* 'Little Missy' | Parent *L. longiflorum* hybrid (2-1 × 4-8) | 'BJM 004' (61-1) | 'BJM 005' (61-2) |
|---|---|---|---|---|
| Plant Height | 25 cm | 27 cm | 30 cm | 40 cm |
| Flower color | Dark pink, speckled with white marks on petals | White (RHSCC Group 155B) | Red (5R V4/C8-10) | Red/Purple (RP V4-5/C8-10) |
| Leaf Count | 80 | 55 avg | 102 avg. | 115 avg. |
| Days to bloom | 120 days | 127 days | 84 days | 90 days |
| Rebloom fall | No | No | Yes | No |
| Rebloom spring | No | Yes | Yes | Yes |

I claim:

1. A new and distinct lily plant as herein illustrated and described.

* * * * *